United States Patent
Huan et al.

(10) Patent No.: US 9,623,065 B2
(45) Date of Patent: Apr. 18, 2017

(54) KIND OF POLYGONUM CAPITATUM EXTRACT, ITS APPLICATION AND A PREPARATION CONTAINING THE POLYGONUM CAPITATUM EXTRACT

(71) Applicant: Zhejiang Sanzheng Biotechnology Co., Ltd., Huzhou (CN)

(72) Inventors: Chen Huan, Huzhou (CN); Chen Zhaorong, Huzhou (CN); Huang Shengwu, Huzhou (CN)

(73) Assignee: ZHEJIANG SANZHENG BIOTECHNOLOGY CO., LTD, Zhejiang (CN)

( * ) Notice: Subject to any disclaimer, the term of this patent is extended or adjusted under 35 U.S.C. 154(b) by 330 days.

(21) Appl. No.: 14/416,086

(22) PCT Filed: Dec. 23, 2013

(86) PCT No.: PCT/CN2013/001625
§ 371 (c)(1),
(2) Date: Jan. 21, 2015

(87) PCT Pub. No.: WO2015/061934
PCT Pub. Date: May 7, 2015

(65) Prior Publication Data
US 2016/0367618 A1    Dec. 22, 2016

(30) Foreign Application Priority Data

Oct. 30, 2013 (CN) .......................... 2013 1 0524219
Oct. 30, 2013 (CN) .......................... 2013 1 0524220
Oct. 30, 2013 (CN) .......................... 2013 1 0532309
Oct. 30, 2013 (CN) .......................... 2013 1 0532321
Oct. 30, 2013 (CN) .......................... 2013 1 0532329

(51) Int. Cl.
*A01N 65/00*    (2009.01)
*A61K 36/704*   (2006.01)
*A61K 36/70*    (2006.01)
*A61K 9/20*     (2006.01)
*A61K 9/16*     (2006.01)
*A61K 9/48*     (2006.01)
*A61K 9/00*     (2006.01)

(52) U.S. Cl.
CPC .......... *A61K 36/704* (2013.01); *A61K 9/1652* (2013.01); *A61K 9/1682* (2013.01); *A61K 9/2054* (2013.01); *A61K 9/4833* (2013.01); *A61K 9/4866* (2013.01); *A61K 36/70* (2013.01); *A61K 9/0095* (2013.01); *A61K 9/48* (2013.01)

(58) Field of Classification Search
CPC ...................................................... A61K 36/00
USPC ....................................................... 424/725
See application file for complete search history.

(56) References Cited

PUBLICATIONS

Liu, Zhijun et al., Chemical Constituents fror Polygonum Capitatum and Their Antioxidation Activities in vitro, Journal of Chinese Medicinal Materials, vol. 31, No. 7, Jul. 2008, pp. 995-998.*

* cited by examiner

*Primary Examiner* — Michael Meller
(74) *Attorney, Agent, or Firm* — Olive Law Group, PLLC (57) ABSTRACT

This invention relates to the preparation of the *Polygonum capitatum* extract and its application and preparation containing the *Polygonum capitatum* extract thereof, belonging to the technical field of Traditional Chinese Medicine. The *Polygonum capitatum* extract is prepared by the following steps: take the dried *Polygonum capitatum*, add the 55~65% ethanol to the dried *Polygonum capitatum*, soak and extract via reflux, and filter and concentrate it to get the concentrate alcohol extract; The drug residue after the alcohol extraction shall be decocted in water, filter and concentrate the water extract, to get the concentrated water extract; merge the concentrated alcohol extract and the concentrated water extract liquid, then concentrate the mixture to obtain the *Polygonum capitatum* extract. The *Polygonum capitatum* extract can be made into tablets, capsules, granules and oral liquid.

2 Claims, 3 Drawing Sheets

KIND OF POLYGONUM CAPITATUM EXTRACT, ITS APPLICATION AND A PREPARATION CONTAINING THE POLYGONUM CAPITATUM EXTRACT

CROSS REFERENCE TO RELATED APPLICATIONS

This application is a 35 USC 371 application of International PCT Patent Application No. PCT/CN2013/001625, filed on Dec. 23, 2013, which claims priority to Chinese Patent Application No. 201310532309.0 filed Oct. 30, 2013, Chinese Patent Application No. 201310524219.7 filed Oct. 30, 2013, and Chinese Patent Application No. 201310532329.8 filed Oct. 30, 2013; all of the contents of which are hereby incorporated by reference herein in their entireties.

TECHNICAL FIELD

The invention relates to the technical field of traditional Chinese medicine, in particular relates to a *Polygonum capitatum* extract and its application and a preparation containing the extract thereof.

BACKGROUND

The *Polygonum capitatum* is originally a folk herbal medicine, is also the Traditional Miao Medicine. Its main efficacies are clearing heat, diuretic, treating stranguria and stopping dysentery. It is mainly used to treat the cystitis, pyelonephritis and dysentery. At present, *Polygonum capitatum* research is mostly focused on the anti-inflammatory activities.

In addition, there are many reports on the preparation of the *Polygonum capitatum* extract, but due to the different extraction methods, the effective ingredients and contents are different. Therefore, technical personnel of this field still expect to get more effective products from the *Polygonum capitatum*.

CONTENT OF THE INVENTION

In view of the problems existing in the prior art, the aim of the invention is designed to provide a technical scheme of *Polygonum capitatum* extract and its application thereof and preparation containing the extracts of *Polygonum capitatum*.

The characteristics of the said extract of *Polygonum capitatum* are obtained by the following steps:

1) Take the dried *Polygonum capitatum* and add 55~65% ethanol soak, and extract via reflux, filter and concentrate it, to obtain the concentrated alcohol extract liquid;

2) After the alcohol extraction the drug residue shall be decocted in water, the decoction liquid is filtered and concentrated, so as to obtain the concentrated water extract liquid;

3) Mix the concentrated alcohol extract liquid and the concentrated water extract liquid, and then concentrate it again, to obtain the *Polygonum capitatum* extract.

A method of preparing the *Polygonum capitatum* extract, wherein its characteristics can be obtained in the said Step 1) through drying as per the following steps: the fresh *Polygonum capitatum* is continuously dried for more than 18 hours under the temperature from −55 to −45° C. and pressure from 15~25 Pa; or the fresh *Polygonum capitatum* is continuously dried for more than 36 hours under the temperature from 40 to 50° C.

A method of preparing the *Polygonum capitatum* extract, wherein its characteristics can be obtained in the said Step 1) through drying as per the following steps: add 55~65% ethanol 22~26 times the amount of the extract, then soak 20 to 40 minutes, and extract for 3 times, each time shall be 1~2 hours, and then merge the extract liquids, filter and concentrate the filtrate to obtain alcohol extract; the drug residue obtained in the alcohol extraction in the said step 2) shall be decocted in water twice, add 10~14 times water the amount of the drug residue in the first time, extract for 1 to 2 hours, in the second time add the water 8~12 times the amount of drug residue, extract for 0.5 to 1 hours, mix the two decoctions, filter and concentrate it, to obtain the concentrated water extract liquid.

The said extract of the *Polygonum capitatum*, which is characterized in the extract that is concentrated to a crude drug equivalent to 0.8~1.2 g/ml in the said step 1), concentrated to a crude drug equivalent to 0.8~1.2 g/ml in the said step 2), and concentrated to a crude drug equivalent to 0.8~1.2 g/ml in the said step 3).

Application of the said *Polygonum capitatum* extract in the preparation of the hypoglycemic drugs.

A described method for preparing a tablet of the *Polygonum capitatum* extract, wherein its characteristics obtained in the process that comprises the following steps:

1) Dry the *Polygonum capitatum* extract to obtain the *Polygonum capitatum* extract powder;

2) Take and weigh the raw materials according to the following weight ratio: the *Polygonum capitatum* extract powder 70~90%, microcrystalline cellulose 10~30%, dextrin 0~10% and low substituted hydroxypropyl cellulose 0~5%;

3) Mix the raw materials prepared in step 2), add ethanol with a concentration of 50~60%, granulate, dry, and obtain the whole particulates;

4) Take the particulates obtained in the Step 3), add magnesium stearate, 0.8~1.2% of total weight, mix and tablet to obtain the hypoglycemic tablets of the extract of *Polygonum capitatum*.

A described preparation method of capsule for the extract of *Polygonum capitatum*, wherein its characteristics in the process that comprises the following steps:

1) Dry the *Polygonum capitatum* extract to obtain the *Polygonum capitatum* extract powder;

2) Take and weigh the raw materials according to the following weight ratio: the *Polygonum capitatum* extract powder 50~80%, the microcrystalline cellulose 15~45%, polyvinylpyrrolidone K30 3~10% and low density hydroxypropyl cellulose, 1~5%;

3) Fully and evenly stir all the raw materials, and place the well-mixed materials in a water bath to heat;

4) Add 60~70° C. hot water and continuously knead the soft material prepared until the color of the mixture is uniform and the soft material has a suitable moisture content;

5) Prepare the pellets by extrusion spheronization machine, the orifice diameter of extruder is 1 mm, the extrusion speed is set to 30~50 rpm/min, the speed of rolling disc is 1000~1400 rpm/min, the spheronization time is 3~5 min, then put the round micro pills into the 40° C. drying oven for 12 h, and then sieve the dry pills to obtain the whole pills;

6) Fill the pills into the capsules with No. 0 capsule filling board, to obtain the hypoglycemic extract capsules of the *Polygonum capitatum*.

A described preparation method of granule for the extract of *Polygonum capitatum*, wherein its characteristics can be obtained in the process that comprises the following steps:

1) Dry the *Polygonum capitatum* extract to obtain the *Polygonum capitatum* extract powder;
2) Mix the *Polygonum capitatum* extract obtained in step 1) with the dextrin, the weight ratio between the *Polygonum capitatum* extract and the dextrin is 1.5 to 2.5:1;
3) Add the intermediate obtained in the step 2) to add ethanol with a concentration of 45 to 55% wherein the weight ratio between the intermediate and ethanol is 4~6:1, and then granulate, bag to obtain the granules of the hypoglycemic extract of *Polygonum capitatum*.

A described method for preparing oral liquid of the extract of *Polygonum capitatum*, wherein its characteristics are in the process that comprises the following steps:

1) Pour the *Polygonum capitatum* extract into the centrifugal with a rotation speed of 800~1200 r/min, for 10~20 min, to obtain supernatant for further use;
2) Take the supernatant obtained in the step 1), use citric acid and sodium carbonate to adjust its pH value to 3.8~6, then add the preservative potassium sorbate, with an amount of 0.04~0.06% the weight of supernatant, and then use distilled water to prepare the liquid medicine: the weight ratio between the herbal and the distilled water is 1:1, and then filter after evenly stirring;
3) Put the prepared liquid in the sterilized dry oral liquid bottle, and seal adequately;
4) Sterilize the oral liquid obtained in the step 3) at 100° C., for 30 to 40 minutes, to obtain the *Polygonum capitatum* extract hypoglycemic oral liquid.

In the present invention the *Polygonum capitatum* extract is obtained via drying, water extraction and alcohol extraction of the *Polygonum capitatum*. The *Polygonum capitatum* extract contains a large number of total flavonoids and total tannins, and the *Polygonum capitatum* extract can improve the insulin resistance of 3T3-L1 fat cells, enhance the ability of fat cells to uptake and utilize glucose, and has a hypoglycemic effect.

In the present invention the *Polygonum capitatum* extract is prepared into the tablet, oral liquid, capsule and granule after reasonable parameters and step condition control, makes it convenient for patients to use, easy to absorb, significantly improve the hypoglycemic function of *Polygonum capitatum* medicinal materials.

SPECIFIC IMPLEMENTATION METHOD

The following embodiments are used to describe the invention further.

Embodiment 1: Preparation of Ethanol and Water Extraction of Fresh *Polygonum capitatum* Extract 1) Add 60% ethanol with 24 times amount of the dried *Polygonum capitatum*, soak for 30 minutes, and extract 3 times, 2 hours each time, merge the extract liquids obtained, then filter and concentrate it to obtain a crude drug equivalent to 1 g/ml, which is the concentrated alcohol extract liquid obtained;
2) The drug residue after the alcohol extraction shall be decocted with water two times. First time add 12 times amount of water and extract for 1.5 hours, second time add 10 times amount of water to extract for 1 hour, and then merge the said two decoction liquids, and then filter and concentrate the liquid obtained to a crude drug equivalent to 1 g/ml, which is concentrated water extract liquid;
3) Merge the alcohol extract and water extract liquids, and then concentrate to a crude drug equivalent to 1 g/ml, which is the *Polygonum capitatum* extract obtained.

The *Polygonum capitatum* in the Step 1) can be obtained by the following steps: Continuously dry the fresh *Polygonum capitatum* at the temperature of −50° C. and the pressure of 20 Pa for 18 hours to get the desired *Polygonum capitatum*.

Embodiment 2: Preparation of the Alcohol Extract and Water Extract of the *Polygonum capitatum*

1) Add 65% ethanol 22 times the amount of the dried *Polygonum capitatum* into the dried *Polygonum capitatum*, soak 40 minutes, and then extract for 3 times, 1 hour each time, and then merge the extract liquids, and then filter and concentrate the merged liquid to obtain a crude drug equivalent to 0.8 g/ml, which is the alcohol extract obtained;
2) The drug residue from the alcohol extraction shall be decocted in water two times, first time add 14 times amount of water, and extract for 1 hour; the second time add 12 times the amount of water, extract for 0.8 hours, merge the two decoctions, and then filter and concentrate it to obtain crude drug equivalent to 0.8 g/ml, which is the water extract obtained;
3) Merge the alcohol extract and water extract liquids, and then concentrate it to a crude drug equivalent to 0.8 g/ml, which is the *Polygonum capitatum* extract.

The *Polygonum capitatum* in the Step 1) can be obtained in the following steps: continuously dry the fresh *Polygonum capitatum* at the temperature of 45° C. for 36 hours.

Embodiment 3: *Polygonum capitatum* Extract Preparation

1) Add 65% ethanol 22 times amount of the dried *Polygonum capitatum* into the *Polygonum capitatum*, soak for 20 minutes, then extract for 3 times, 1 hours each time, and then merge the extract liquids, and then filter and concentrate it to obtain a crude drug equivalent to 1 g/ml, which is the alcohol extract obtained;
2) The drug residue from the alcohol extraction shall be decocted in water for two times, first time, add water 10 times the amount of the drug residue, extract for 2 hours, second time add water 12 times the amount of the drug residue, extract for 0.5 hours, then merge the two decoctions, filter and concentrate it to obtain a crude drug equivalent to 1 g/ml, which is the water extract obtained;

3) Merge the alcohol extract and water extract liquids, and then concentrate it to a crude drug equivalent to 1 g/ml, which is the *Polygonum capitatum* extract obtained.

The *Polygonum capitatum* in the Step 1) can be obtained by the following steps of drying: Continuously dry the fresh *Polygonum capitatum* under the temperature of −45° C. and the pressure of 25 Pa 24 hours, or continuously dry the fresh *Polygonum capitatum* under the temperature of 40° C. for 40 hours.

Embodiment 4: *Polygonum capitatum* Extract Preparation

1) Add 55% ethanol, 26 times the amount of dried *Polygonum capitatum* into the dried *Polygonum capitatum*, soak 40 minutes, and then extract for 3 times, 1.5 hours each time, and then merge the extract liquids, then filter and concentrate it to obtain a crude drug equivalent to 1.2 g/ml, which is the alcohol extract;

2) The drug residue after the alcohol extraction shall be decocted twice. In the first time, add water 14 times the amount of the drug residue, extract for 1.5 hours; in the second time add water 8 times the amount of drug residue, extract for 0.8 hours, and then merge the liquids, filter and concentrate it to obtain a crude drug equivalent to 1.2 g/ml, which is the concentrated water extract obtained;

3) Merge the concentrated alcohol extract and concentrated water extract, and then concentrate it to a crude drug equivalent to 1.2 g/ml, which is the *Polygonum capitatum* extract obtained.

The *Polygonum capitatum* in the Step 1) can be prepared in the following steps: continuously dry the fresh *Polygonum capitatum* at the temperature of −55° C. and the pressure of 15 Pa for 36 hours, or continuously dry the fresh *Polygonum capitatum* at the temperature of 50° C. for 50 hours.

Contrasting Embodiment 1: Preparation of the Alcohol Extraction from Fresh and Dry *Polygonum capitatum* Extract The dried *Polygonum capitatum* is soaked in 60% ethanol 24 times the amount of material for 30 min, and extract it via reflux in the water bath for 3 times, each time 2 hours, merge the filtrates, concentrate it to the desired concentration. The *Polygonum capitatum* can be obtained by the steps of drying: continuously dry the fresh *Polygonum capitatum* at the temperature of −50° C. and the pressure of 20 Pa for 18 hours, or continuously dry the fresh *Polygonum capitatum* at the temperature of 45° C. for 36 hours to obtain the dried *Polygonum capitatum*.

Contrasting Embodiment 2: Preparation of the Water Extraction from Fresh and Dry *Polygonum capitatum* Extract The dried *Polygonum capitatum* is soaked in water for 30 min, and decocted in water for two times. In the first time, add water 12 times amount of the drug, keep weak boiling for 1.5 hours; in the second time, add water 10 times amount of the drug, and keep boiling for 1 hours, and then merge the filtrates, concentrate it to the desired concentration. The *Polygonum capitatum* can be obtained by the steps of drying: continuously dry the fresh *Polygonum capitatum* at the temperature of −50° C. and the pressure of 20 Pa for 18 hours, or continuously dry the fresh *Polygonum capitatum* at a temperature of 45° C. for 36 hours to obtain the dried *Polygonum capitatum*.

Test Case 1: Fresh GCP Lyophilization Process and GCP Drying Process

The main influence factors of GCP lyophilization process is the lyophilization time, the moisture content of material is about 3-5% after the lyophilization. In this experiment, the frozen drug moisture content not exceeding 4% as the index, the single factor is adopted to measure the lyophilization time.

Precisely weigh the GCP 100 g and place it in a freeze dryer (temperature: −50±5° C., the pressure: 20±5 Pa), determine the moisture contents of the drugs after drying for 6 h, 12 h, 18 h and 24 h respectively. The results obtained are shown in Table 1.

TABLE 1

| Item | Lyophilization time (h) | Moisture content (%) |
|---|---|---|
| 1 | 6 | 8.620 |
| 2 | 12 | 5.970 |
| 3 | 24 | 3.885 |
| 4 | 36 | 2.554 |

Results: The moisture content of the GCP can meet the requirements after it is continuously dried in freeze-drying instrument (temperature: −50±5° C., the pressure: 20±5 Pa) for 18 h, the Lyophilized GCP hereinafter is called as the fresh GCP.

2. GCP Drying Process

The main influence factors of the GCP drying process are the drying time and drying temperature. In order to keep the medicinal properties in the greatest degree from damaging, this experiment chooses 45° C. as the drying temperature, the moisture content of drug after drying not more than 4% as the index, the drying time is measured by single factor. The results obtained are shown in Table 2.

TABLE 2

| Item | Drying time (h) | Moisture content (%) |
|---|---|---|
| 1 | 6 | 14.930 |
| 2 | 12 | 10.235 |
| 3 | 24 | 7.884 |
| 4 | 36 | 3.182 |

Results: The moisture content of the GCP can conform to the requirements after it is continuously dried in the electric air blowing drying box (temperature: 45±5° C.) for 36 h, hereinafter the GCP is called as the dried GCP.

Test Case 2: A Comparative Study of Total Flavonoids Content in the Dried and Fresh GCP 1 Methods and Results 1.1 Methods 1.1.1 Preparation and processing of sample: Take 3 g GCP medicinal herbs (10 mesh), add 90 ml of water, reflux in the water bath for 1 hour, and then filter it (protect it from light), take the successive filtrate, which the solution obtained for further use.

1.1.2 Preparation of gallic acid control solution: Precisely weigh the control product of gallic acid 5.0 mg, place it into a 10 ml Brown volumetric flask, dilute it to the volume with distilled water, dissolve in ultrasonic, take 2.5 ml solution from the 10 ml Brown volumetric flask to a 50 ml Brown volumetric flask, which is 0.025 mg/ml of gallic acid standard solution obtained.

1.1.3 Selection of wavelength determination: Precisely take 3.3 ml gallic acid control solution, place it into a 25 ml Brown volumetric flask, then add 1 ml of phosphorus molybdenum sodium tungstate (prepared in the laboratory, with reference to Chinese Pharmacopoeia 2010 Edition) and then add the distilled water to 13 ml, add 29% sodium carbonate solution to the scale, gently shake to even, keep without shaking for 30 min, then place into 1 cm cuvette, use the accompanying reagents as blank group, then scan in 400~900 nm, a maximum absorption at the wavelength of 758 nm can be found.

1.1.4 Plotting the standard curve: Precisely take the reference solution 1.5, 2.5, 3.5, 4.5, 5.5, 6.5 ml into the 25 ml Brown volumetric flask, operate at the maximum absorption wavelength according to the "1.1.3". Use the concentration (C) and the light absorption value (A) to conduct the linear regression, to obtain the linear regression equation and correlation coefficient, and the regression equation Y=102.57X+0.0286 (r=0.9995), the results show that the gallic acid in 0.0015~0.0065 mg/ml and absorbance have a good linear relationship.

1.1.5 Determination of total phenol: Precisely take 1.5 ml solution prepared into a 50 ml Brown volumetric flask, precisely take 2 ml into a 25 ml Brown volumetric flask. Prepare as per the "1.1.3", determine the absorbance, and take it into the linear regression equation obtained to calculation the result.

1.1.6 Determination of non-absorbed polyphenols: Precisely take 2 ml solution prepared, and place it into a 50 ml corked cone flask containing 0.6 g casein, add water to 10 ml, and tightly plug the cork, then place into 30° C. water bath for heat insulation for 1 hour, and continuously shake, then filter precisely take 2 ml successive filtrate, place it into a 25 ml Brown volumetric flask, and prepare according to the method of "1.1.4" linear relation, determine the absorbance values, and take the value into the linear regression equation obtained, to calculate the result.

1.1.7 Determination of total tannin content: total tannin content=total phenolic−non-absorbed polyphenol content.

1.1.8 Test of precision: Accurately absorb 4 ml gallic acid control solution into a 25 mL Brown volumetric flask, determine the absorbance according to the method of 1.1.3, RSD 0.89%.

1.1.9 Stability test: Precisely take 1.5 ml solution prepared into a 50 ml Brown volumetric flask, then precisely take 2 ml solution into a 25 ml Brown volumetric flask, determine the absorbance as per the method of "1.1.3", stabilize it within 10 min, RSD 1.24%.

1.1.10 Repeatability test: Extract as per "1.1.1", precisely take 1.5 ml solution prepared into a 50 ml Brown volumetric flask, and precisely take 2 ml solution prepared into a 25 ml Brown volumetric flask, determine the absorbance as per the method of "1.1.3", and determine the total phenolic content as per the method of "1.1.6", determine the absorbance non-absorbed polyphenol content, its RSD is 1.75% (n=6), which shows a good repeatability in determination of total tannin.

1.1.11 Recovery rate test: Precisely take 6 parts of sample with known total tannin content in the same batch, into a 25 ml Brown volumetric flask, precisely add 0.041 mg gallic acid control products respectively, determine the total phenolic content as per the method of "1.1.3", its RSD 2.26%, the results are listed in Table 3

TABLE 3

Recovery experiment of total phenolic of the GCP extract

| The total tannin content of sample solution/mg | Determination rate/mg | Recovery rate/% | Average recovery rate/% |
|---|---|---|---|
| 0.1051 | 0.1452 | 97.80 | 97.32 |
| 0.1051 | 0.1466 | 101.22 | |
| 0.1053 | 0.1451 | 97.07 | |
| 0.1042 | 0.1432 | 95.12 | |
| 0.1020 | 0.1411 | 95.37 | |
| 0.1010 | 0.1409 | 97.32 | |

According to Preparation method of the "1.1.10", determine and compare (n=6) the total tannin contents of the fresh GCP and dried GCP. The results are shown in Table 4.

TABLE 4

Total tannin contents of the fresh GCP and the dried GCP, (n = 6)

| GCP | The total tannin content/ mg · g$^{-1}$ | Average content of total flavonoids/mg · g$^{-1}$ |
|---|---|---|
| Fresh GCP | 50.69 | 51.52 |
| | 50.55 | |
| | 50.52 | |
| | 51.49 | |
| | 51.74 | |
| | 54.11 | |
| Dry GCP | 46.97 | 46.39 |
| | 47.02 | |
| | 46.92 | |
| | 46.55 | |
| | 45.66 | |
| | 45.20 | |

From Table 4 it can be seen that the total tannin content of fresh GCP is higher than that of the dried GCP, i.e. 1.11 times.

Test Case 3: Comparison of the Hypoglycemic Effects of the Fresh and Dried GCP Based 3T3-L1 Cells 1 Experimental Method 1.1 Cell Culture 3T3-L1 mouse embryonic fibroblast cells, are derived from the Institute of Life Science of Chinese Academy of Sciences. Plant the 3T3-L1 preadipocytes into the 25 cm2 cell culture plate, add 6 ml normal culture medium, keep it at culture conditions of 37° C. and 5% $CO_2$, change liquid in the next day. Pass or store it in freezing conditions after the 80% cell fused.

1.2 Induced Differentiation of the Cells

Inoculate the 3T3-L1 preadipocytes at the density of $5 \times 10^3$ in a 24-hole culture plate, wait until the cells grow to contact inhibition, replace the cell culture medium with differentiation liquid A (0.5 mmol/L IBMX, 0.1 umol/L DEX, 10 mg/L INS) and culture them for 48 h, then replace with the induction differentiation liquid (10 mg/L) to continuously culture for 48 h B, change the normal culture medium to continue culturing, and change the liquid once every 2 days, 90% of the above induced differentiation cells will have a mature phenotype after 6-8 days.

1.3 IR Model Preparation

After counting the 3T3-L1 cells in logarithmic growth phase, inoculate them at the density of $5*10^3$ each hole onto 24-hole culture plate, then put the culture plate into the $CO_2$ incubator, under the conditions of a temperature of 37° C., 5% $CO_2$ and saturated humidity, culture them to growth inhibition, induction differentiation to mature adipocytes. Add the following processing factors:

The control group shall be continued with their normal culture medium (DMEM high glucose culture liquid containing 10% FBS)

The model group shall be given 1 umol DEX normal culture medium;

Other cells shall be used in each drug group experiment 1.4 Influence on the Proliferation of 3T3-L1 Preadipocyte (MTT Method)

Collect the 3T3-L1 preadipocytes in the logarithmic growth phase, adjust the cell suspension concentration, with a density of $5\times10^3$ at each hole inoculated into 96-hole plate, add 100 ul to each hole. Put the cells under the conditions of 37° C. and 5% $CO_2$ saturated humidity CO2 incubator and culture to 80% cell fusion, then add 100 ul the high, medium and low three concentrations of medicine into each hole, set 4 holes, at the same time set blank control and normal control, in 3 parallel plates. Continuously culture 48 h, observe under inverted microscope. Each hole is added with 20 ulMTT solution (5 mg/ml), incubate for 4 h. Then terminate the culture, be careful to absorb the culture liquid in the holes. Each hole is added with 150 ulDMSO, and place it in shaking bed to vibrate for 10 min, to fully dissolve the crystalline. Determine the absorbance OD values in each hole in the microplate reader at the wavelength of 490 nm. Then calculate the change of 3T3-L1 preadipocyte proliferation rate.

The cell survival rate=(OD test group−OD blank group)/(OD control group−OD blank group)*100%. When the survival rate is greater than 80%, it shows that the drug does not inhibit the proliferation of cells.

1.5 Influence of Glucose Utilization on the 3T3-L1 Adipocyte Insulin Resistance (IR) Model After counting the 3T3-L1 cell in logarithmic growth phase, inoculate each hole with density of $5\times10^3$ cells in 24-hole culture plate. According to the IR models preparation method of 2.3, divide the mature 3T3-L1 adipocytes into a normal culture group and model group, the model group can also be divided into a model control group and each drug group. The model group shall be given 1 umol DEX to react for 48 h. After the models are built, administer the drug as per the experimental groups and the concentration of drug, in 3 parallel plates. In 24 h, 48 h the cell morphologies shall be observed and take the supernatant to be tested on the semi automatic biochemical instrument, determine the glucose (GLU) content in the culture solution according to the descriptions of the kit.

2 the Results of Experiment 2.1 The influence on the proliferation of 3T3-L1 preadipocyte is shown in Table 5. The dried GCP water extraction and the fresh GCP water extraction in the test case are obtained via the method in the contrasting Embodiment 2. The dried GCP alcohol extraction and the fresh GCP alcohol extraction in the test case are obtained via the method in the contrasting Embodiment 1. The dried GCP alcohol and water extraction is prepared via the method the Embodiment 2, and the dried GCP alcohol and water extraction is obtained via the method the Embodiment 1.

TABLE 5

Influence on the 3T3-L1 cells growth

| Group | Concentration/ (ug/ml) | Average absorbance | Cell survival rate % |
|---|---|---|---|
| Dried GCP water extract liquid | 100 | 2.571 | 82.23% |
|  | 25 | 2.948 | 95.67% |
|  | 6.25 | 2.893 | 93.70% |
| Dried GCP alcohol extract liquid | 100 | 2.489 | 79.31% |
|  | 25 | 2.752 | 88.67% |
|  | 6.25 | 2.993 | 97.25% |
| Dried GCP alcohol and water extract liquid | 100 | 2.970 | 96.43% |
|  | 25 | 3.062 | 99.71% |
|  | 6.25 | 2.949 | 95.70% |
| Fresh GCP water extract liquid | 100 | 2.799 | 90.36% |
|  | 25 | 2.663 | 85.52% |
|  | 6.25 | 3.042 | 99.00% |
| Fresh GCP alcohol extract liquid | 100 | 3.149 | 102.83% |
|  | 25 | 3.113 | 101.53% |
|  | 6.25 | 2.627 | 84.23% |
| Fresh GCP alcohol and water extract liquid | 100 | 2.977 | 96.68% |
|  | 25 | 2.753 | 88.73% |
|  | 6.25 | 2.964 | 96.21% |

Table 5 shows that the cell survival rate is basically more than 80%, indicating that each drug concentration has no significant inhibitory effect on the proliferation of cells. 100 ug/ml, 25 ug/ml and 6.25 ug/ml can be used as the high, medium and low concentrations to further investigate the hypoglycemic effect of different components.

2.2 Influence of Glucose Utilization on the 3T3-L1 Adipocyte IR Model is Shown in Table 6.

TABLE 6

Influence of glucose utilization on the adipocytes IR model

| Group | Concentration/ (ug/ml) | Average 24 h GLU content/ (mmol/l) | Average 48 h GLU content/(mmol/l) |
|---|---|---|---|
| Normal control group | — | 20.95 | 21.00 |
| Model control group | — | 23.08 | 22.18 |
| Positive drug (ROG) | 50 | 21.84 | 20.53 |
|  | 12.5 | 22.04 | 21.67 |
|  | 3.125 | 22.24 | 20.46 |
| Normal control group | — | 24.70 | 23.25 |
| Model control group | — | 27.72 | 26.27 |
| Positive drug (ROG) | 100 | 25.38 | 24.64 |
| Dried GCP water extract liquid | 100 | 26.92 | 26.07 |
| Dried GCP alcohol extract liquid | 100 | 25.94 | 25.99 |
| Dried GCP alcohol and water extract liquid | 100 | 25.71 | 25.81 |
| Fresh GCP water extract | 100 | 25.26 | 25.25 |
| Fresh GCP alcohol extract liquid | 100 | 25.09 | 24.45 |
| Fresh GCP alcohol and water extract liquid | 100 | 24.73 | 24.02 |

We can see that from Table 6, comparison of hypoglycemic effects of the fresh GCP and dried GCP medicinal water extract, alcohol extract, and water and alcohol extract, under the same extraction method, the hypoglycemic effect of the fresh GCP extract is higher than that of dried GCP. At the same time, the effect of the water and alcohol extract is better than that of the alcohol extract alcohol, hypoglycemic effect of the alcohol extract parts is better than that of the water extract.

Test Case 4: Comparison of Hypoglycemic Effects of Alcohol GCP Extract, Water GCP Extract, and Alcohol Water GCP Extract Based Animal and Cells.

1. Experimental Method

Comparison of hypoglycemic effects of alcohol GCP extract, water GCP extract, and alcohol water GCP extract based animal and cells.

1.1 Drug Extraction

Alcohol extraction: Please refer to the contrasting Embodiment 1.

The dried *Polygonum capitatum* is soaked in 60% ethanol 24 times amount of it for 30 min, extract via reflux in the water bath for 3 times, each time 2 hours, and then merge the filtrates, and concentrate the filtrate obtained to the desired high dose concentration (1 g/ml).

Water extraction: please refer to the contrasting Embodiment 2.

The dried *Polygonum capitatum* is soaked in water for 30 min, and then add water to decoct for two times. In the first time, add water 12 times as the drug amount, and keep in weak boiling 1.5 hours, in the second time, add water 10 times the amount of medicine, and keep in a low boil for 1 hours, and then merge the filtrates, concentrated the filtrate obtained to the desired high dose concentration (1 g/ml).

Alcohol and water extraction: please refer to the Embodiment 1.

1) The dried *Polygonum capitatum* is soaked in 60% alcohol, 24 times the amount of the drug, for 30 min, and extract it for three times. 2 hours for each time. Then merge the extract liquids, concentrate the liquids obtained to a crude drug equivalent to 1 g/ml, which is the concentrated alcohol extract liquid obtained;

2) The drug residue after the alcohol extraction shall be decocted in water for two times. In the first time, add water 12 times the amount of the drug residue, extract for 1.5 hours; in the second time add water 10 times the amount of the drug residue, extract for 1 hour; and then merge the two decoction liquids, and filter and concentrate it to obtain a crude drug equivalent to 1 g/ml, which is the concentrated water extract;

3) Merge the concentrated alcohol extract and concentrated water extract, and then concentrate it to a crude drug equivalent to 1 g/ml, which is the *Polygonum capitatum* extract obtained.

1.2. Animal Experiment 1.2.1 Modeling

Take 460 KM mice, with a weight of (20±2) g, half male and half female, let them to adapt to the environment for 7 days. Randomly select 6 male mice and 6 female mice as the blank control group, keep them fasted but water is supplied to them for 18 hours, use the physiological saline to prepare the 1.1% alloxan, and store it in an ice water bath. Carry out the intraperitoneal injection according to the ratio of 110 mg/kg, the control group is injected with the isodose physiological saline, let them eat after 1 h recovery. Use the same modeling method in the second day. 3 days later (72 h, normal diet), then fasting 12 hours, and then cut their tails to take a few drops of blood, and then fasting blood glucose is measured with glucose oxidase method, the mice with the blood glucose value greater than 11.1 mmol/L are the mice that successfully modeled.

1.2.2 Modeling Results

Among the 460 KM mice, 12 of them belong to the blank control group, the remaining mice are used to modeling. After the modeling the mice with the blood glucose values measured greater than 11.1 mmol/L. In the design process each experimental group has 12 mice. The experimental results show that the number of female mice is larger, so the number of doses of female mice is designed to be only 6-8 (8 mice have the statistical significance), individual model mouse-tail is damaged, which is not conducive to take the blood sample, it is not designed in this experimental group. The actual modeling success rate was 48.03%, and the mortality was 1.75%.

1.2.3 Experimental Groups

Take the model mice, randomly divide then into 16 groups, namely the water extraction (high, medium and low) dose group, the alcohol extraction (high, medium and low) dose group, the water and alcohol extraction (high, medium and low) dose group, the modeling group, positive group and blank control group (normal mice), please refer to Table 1.

1.2.4 Determination of the Blood Glucose

Use surgical scissors to cut 2-3 mm of a mouse tail, press the tail to take a few drops of blood and place in the EP tube, first add 12 μL 15 g/L bipotassium EDTA solution, high speed centrifuge it (10000 r/min) for 5 min. Wait till the blood is stratified, take the upper layer serum 10 μL, plus 30 μL physiological saline, shake it evenly; and take 10 μL the dilute serum and put into a EP tube, add 1 mL glucose (Glu) oxidase, shake it evenly, keep at 37° C. for 15 min, the sample (U) is to be measured. Then take the physiological saline and calibrator (c) 10 μL respectively, add 1 mL glucose oxidase, shake evenly, keep at 37° C. for 15 min, determine the absorbance (A) with 505 nm wavelength after adjusting the blank tube to zero.

Sample of Glu (mmol/L)=Au/Ac*Cc 1.2.5 Experimental Results and Discussion

Determine the fasting blood glucose values corresponding to the administration of 7 d, 14 d, 21 d, 28 d after the success of modeling (fasted but water is supplied for 12 h). Table 1 is the influence of the compositions of the pieces on the mice blood glucose concentration of hyperglycemia model.

The alloxan has a particularly destructive effect on insulin beta cells, resulting in low secretion, which leads to the animal experimental alloxan diabetes. This experiment adopts the GOD-POD method for determination of serum glucose concentration, the principle of this method is POD in serum glucose is oxidized into D-gluconic acid in the presence of GOD, and generate $H_2O_2$; the latter and 4-amino antipyrine and phenol form red benzophenone imine under the effect of peroxidase (POD) benzophenone imine, the depth of the color of the ketone compounds is directly proportional to the content of glucose. Determine the absorbance values of the standard tube and the sample tube respectively, and then calculate the content of glucose.

We can see from Table 7 that the water extraction group, the alcohol extraction group, and water and alcohol extraction group, and the positive group showed a hypoglycemic effect, the effect of water and alcohol extraction was significantly better than that of the other GCP extraction method.

TABLE 7

Influence of compositions of pieces on the mice blood glucose concentration of the hyperglycemia mode

| Group | Quantity | Dose/(g/20 g) | Blood glucose level/(mmol/l) | | | |
|---|---|---|---|---|---|---|
| | | | 7 d | 14 d | 21 d | 28 d |
| High dose of the alcohol GCP extract | 12 | 0.4 | 17.42 ± 6.2 | 21.88 ± 5.92 | 23.05 ± 4.80* | 25.11 ± 9.60 |
| Medium dose of the alcohol GCP extract | 14 | 0.2 | 15.99 ± 5.96* | 20.68 ± 12.26 | 17.70 ± 8.72* | 21.92 ± 10.37 |
| Low dose of the alcohol PCP extract | 13 | 0.1 | 16.79 ± 5.95 | 18.11 ± 6.22 | 20.87 ± 5.57* | 26.64 ± 8.52 |
| High dose of the water GCP extract | 12 | 0.4 | 19.45 ± 5.00 | 18.93 ± 5.76 | 24.73 ± 7.89 | 25.27 ± 8.87 |
| Medium dose of the water GCP extract | 14 | 0.2 | 20.71 ± 4.83 | 19.81 ± 6.98 | 24.45 ± 8.99 | 26.36 ± 9.24 |
| Low dose of the water PCP extract | 14 | 0.1 | 18.66 ± 5.67 | 20.59 ± 6.97 | 20.63 ± 5.71* | 27.63 ± 9.25 |
| High dose of GCP alcohol and water extract | 14 | 0.4 | 19.16 ± 7.66 | 19.84 ± 7.25 | 19.41 ± 7.83* | 21.76 ± 9.68* |
| Medium dose of GCP alcohol and water extract | 13 | 0.2 | 15.94 ± 5.32* | 16.78 ± 6.74* | 19.02 ± 8.37* | 21.33 ± 8.31* |
| Low dose of GCP alcohol and water extract | 12 | 0.1 | 17.63 ± 7.10 | 18.26 ± 7.28 | 18.82 ± 8.88* | 19.90 ± 10.11* |
| Model group (Physiological saline) | 12 | 0.4 ml | 20.41 ± 5.66 | 21.80 ± 4.96 | 26.93 ± 2.84 | 28.63 ± 4.51 |
| Positive group (Acarbose) | 12 | 0.5 mg | 19.23 ± 7.54 | 18.00 ± 6.99 | 19.99 ± 6.69 | 22.81 ± 7.72 |
| Blank control group (Physiological saline) | 12 | 0.4 ml | 5.15 ± 1.58 | 7.99 ± 1.48 | 7.43 ± 1.47 | 8.08 ± 1.99 |

Figure 1:
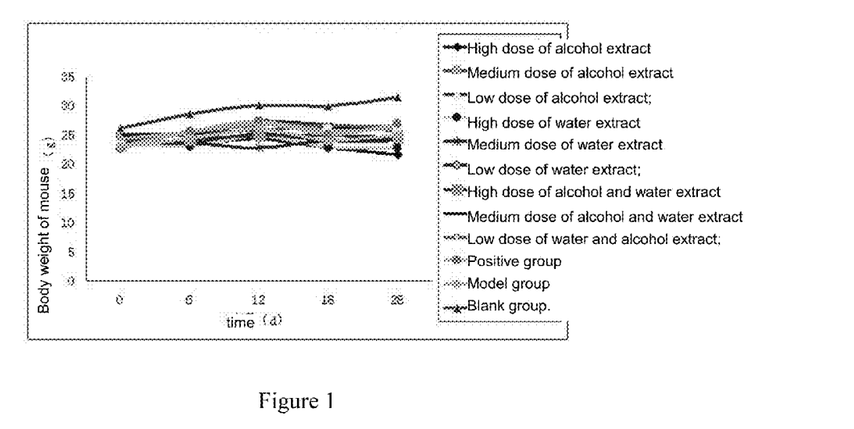
FIG. 1 A comparison chart of the effects of different extracts on body weight of mice.

And we can see from FIG. 1 that, after 18 days of treatment, the body weight of the mice administered with the alcohol and water extraction (medium and low) doses are higher than that in the model group, the body weight of the mice of the positive group is higher than that of model group.

Figure 2:
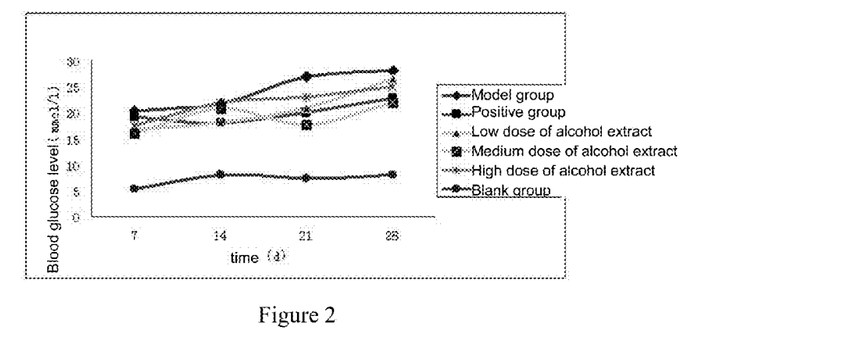
FIG. 2 Pharmacodynamic Effect Comparison chart of the alcohol extract on different dose of decoction tablets.

We can see from FIG. 2 that, compared to the modeling group, the pieces of the alcohol extract has a certain hypoglycemic effect. After the administration for 21 days, the alcohol extraction group compared with model group, has an obvious hypoglycemic effect, and the hypoglycemic effect of the medium dose group of the alcohol extract group is better than that of the high dose group and low dose group.

Figure 3:
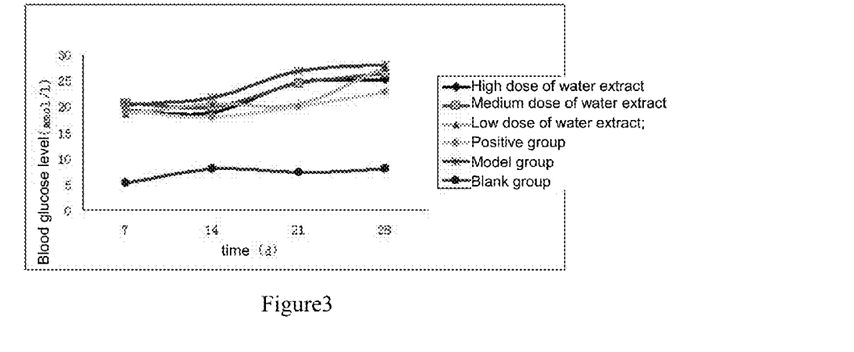
FIG. 3 Pharmacodynamic Effect Comparison chart of the water extract on different dose of decoction tablets.

We can see from FIG. 3 that, compared to the modeling group, the pieces of the water extract has a certain hypoglycemic effect, but its effect is weaker than that of the positive drug. After administering for 28 days, compared to the modeling group, the blood glucose of each dose group of the water extract is close, shows no significant trend.

Figure 4:
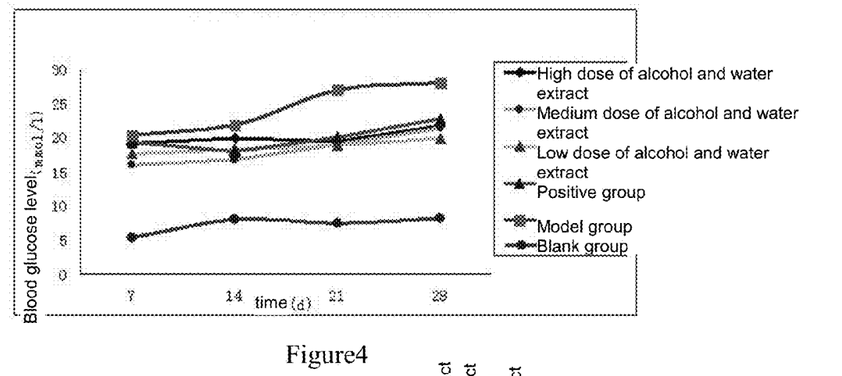
FIG. 4 Pharmacodynamic Effect Comparison chart of the water and alcohol extract on different dose of decoction tablets.

We can see from FIG. 4 that, compared to the modeling group, the alcohol and water extract liquid has a significant hypoglycemic effect, and after 21 days of treatment it is more obvious, at this time, the effects of each dose group is higher than that of the positive drug, and each dose group also shows no significant trend.

Figure 5:
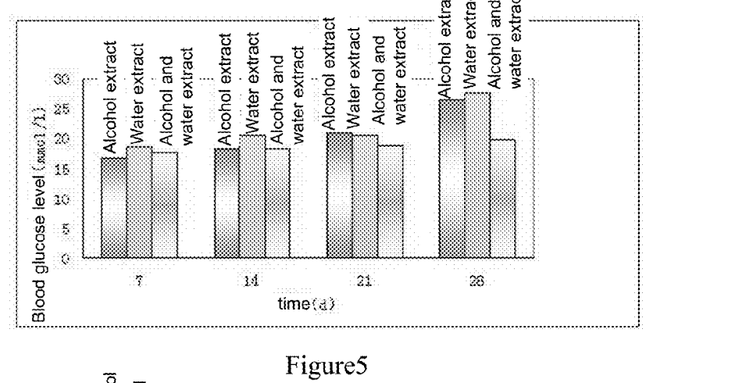
FIG. 5 Pharmacodynamic Effect Comparison chart of the different extraction methods.

We can see from FIG. 5 that, the different extraction method has a significant effect on the hypoglycemic effect of decoction pieces. With the prolongation of the dosing time, the hypoglycemic effect of the alcohol and water extract is significantly higher than that in water extract and alcohol extract. The hypoglycemic effect of the alcohol extract ranks second, and that of the water extract is the worst, but no significant difference between the said two.

Figure 6:
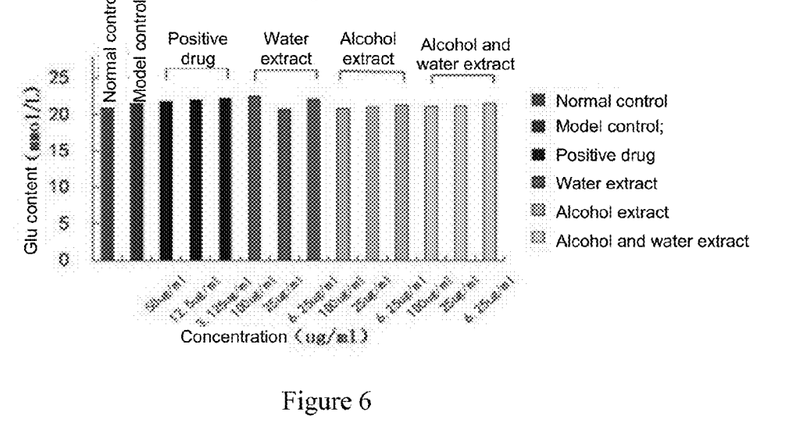
FIG. 6 Chart of glucose consumption by the supernatant obtained by different extraction method and delivered to the cells in 24 hours.

We can see from FIG. 6 that, after the different extracts are applied to the cells for 24 h, the extracts obtained via three extraction methods can reduce the blood sugar, wherein the hypoglycemic effect of the alcohol and water extract, and alcohol extract is better than that of the water extract.

Figure 7:
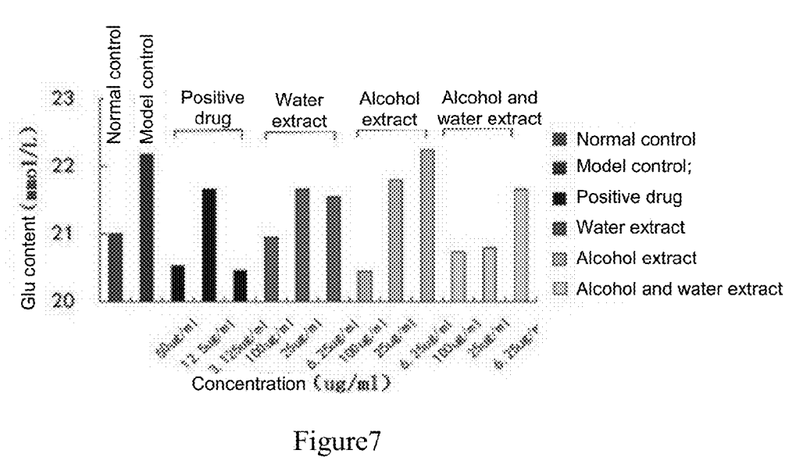
FIG. 7 Chart of glucose consumption by the supernatant by different extraction method and delivered to the cells in 48 hours.

We can see from FIG. 7 that, after the different extracts are applied to the cells for 48 h, the extracts obtained via three extraction methods can reduce the blood sugar, wherein the hypoglycemic effect of high doses of the alcohol and water extract, and alcohol extract is better than that of high doses of the water extract, and with the increase of the dose, the hypoglycemic effect increases.

Embodiment 5: Preparation of Tablets of the *Polygonum capitatum* Antidiabetic Extract 1) Dry the *Polygonum capitatum* extract obtained the Embodiment 1-4 to prepare the *Polygonum capitatum* extract powder;
2) Take and weigh the raw materials according to the following weight ratio: the *Polygonum capitatum* extract powder 80%, microcrystalline cellulose 10%, dextrin 5% and low substituted hydroxypropyl cellulose 5%;
3) Mix the raw materials prepared as per step 2), and add the ethanol with a concentration of 55%, the amount of ethanol added is 18% of the total raw materials, and granulate, dry, and obtain the granules;
4) Take the granules obtained as per step 3), and add the magnesium stearate, with an amount of 1% the total weight of the granules, evenly mix, tablet, to obtain the *Polygonum capitatum* antidiabetic extract tablet.

Embodiment 6: Preparation of Tablets of the *Polygonum capitatum* Antidiabetic Extract 1) Dry the *Polygonum capitatum* extract obtained the Embodiment 1-4 to prepare the *Polygonum capitatum* extract powder;

2) Take and weigh the raw materials according to the following weight ratio: the *Polygonum capitatum* extract powder 70%, microcrystalline cellulose 20%, dextrin 8% and low substituted hydroxypropyl cellulose 2%;

3) Mix the raw materials prepared as per step 2), and add the ethanol with a concentration of 60%, the amount of ethanol added is 15% of the total weight of the raw materials, and granulate, dry, and obtain the granules;

4) Take the granules obtained as per step 3), and add the magnesium stearate, with an amount of 0.8% the total weight of the granules, evenly mix, tablet, to obtain the *Polygonum capitatum* antidiabetic extract tablet.

Embodiment 7: Preparation of Tablets of the
*Polygonum capitatum* Antidiabetic Extract 1) Dry the *Polygonum capitatum* extract obtained the Embodiment 1-4 to prepare the *Polygonum capitatum* extract powder;

2) Take and weigh the raw materials according to the following weight ratio: the *Polygonum capitatum* extract powder 90%, microcrystalline cellulose 10%;

3) Mix the raw materials prepared as per step 2), and add the ethanol with a concentration of 50%, the amount of ethanol added is 20% of the total raw materials, and granulate, dry, and obtain the granules;

4) Take the granules obtained as per step 3), and add the magnesium stearate, with an amount of 1.2% the total weight of the granules, evenly mix, tablet, to obtain the *Polygonum capitatum* antidiabetic extract tablet.

Test Case 5: Testing the Efficacy of the *Polygonum capitatum* Hypoglycemic Extract Tablet
1 Experimental Methods
Efficacy test of the *Polygonum capitatum* hypoglycemic extract tablet
1.1 Experimental Drugs
Preparation of the *Polygonum capitatum* hypoglycemic extract tablets through the Embodiment 5, 6 or 7.
1.2. Animal Experiment
1.2.1 Modeling Take 80 KM mice, with a body weight of (20+2) g, half male and half female, and let them to adapt to the environment for 7 days. Randomly select 6 male mice and female mice as the blank control group, fasted and supplied with water for 18 h. Prepare 1.1% alloxan with physiological saline, and keep it in ice water bath. Carry out intraperitoneal injection according to a dose of 110 mg/kg, the mice of the control group are to be injected with physiological saline, and then fast them 12 hours, use the same modeling method in the second day. 3 days later (72 h, restore to normal diet), then fast 12 h, and then cut the tail to take a few drops of blood. The fasting blood glucose was measured with glucose oxidase method. The mice that have a blood glucose value greater than 11.1 mmol/L are mice that have been successfully modeled.

1.2.2 Modeling Results

Among the 80 KM mice, 12 are as the blank control group, the remaining mice are used to modeling. After modeling, find the mice with the blood glucose values measured more than 11.1 mmol/L. In the experiment design process each group is set with 12 mice, the number of female mice are larger in the experimental results, so the number of female mice designed a dose is 6-8 only (8 with only statistical significance), the tails of some of the male model mice may be damaged, which is not conducive to the blood sampling in the next step, therefore it is not designed in this experimental group. The actual modeling success rate is 48.03%, the mortality is 1.75%.

1.2.3 Experimental Groups

Take the model mice, randomly divide then into 6 groups, namely the pieces (high, medium and low) dose group, the modeling group, positive group and blank control group (normal mice), each group has 6 mice, half male and half female. Please refer to Table 8.

1.2.4 Determination of the Blood Glucose

Use surgical scissors to cut 2-3 mm of a mouse tail, press the tail to take a few drops of blood and place in the EP tube, first add 12 μL 15 g/L bi-potassium EDTA solution, high speed centrifuge it (10000 r/min) for 5 min. Wait till the blood is stratified, take the upper layer serum 10 μL, plus 30 μL physiological saline, shake it evenly; and take 10 μL the dilute serum and put into a EP tube, add 1 mL glucose (Glu) oxidase, shake evenly, keep at 37° C. for 15 min, the sample (U) is to be measured. Then take the physiological saline and calibrator (c) 10 μL respectively, add 1 mL glucose oxidase, shake it evenly, keep at 37° C. for 15 min, determine the absorbance (A) with 505 nm wavelength after adjusting the blank tube to zero.

$$\text{Sample Glu (mmol/L)} = Au/Ac \cdot Cc$$

1.2.5 Experimental Results and Discussion

Determine the fasting blood glucose values corresponding to the administration of 7 d, 14 d, 21 d and 28 d after the success of modeling (fasted but water is supplied for 12 h). Table 8 is the influence of the compositions of the pieces on the mice blood glucose concentration of hyperglycemia model.

The alloxan has a particularly destructive effect on insulin beta cells, resulting in low secretion, which leads to the animal experimental alloxan diabetes. This experiment adopts the GOD-POD method for determination of serum glucose concentration, the principle of this method is POD in serum glucose is oxidized into D-gluconic acid in the presence of GOD, and generate $H_2O_2$; the latter and 4-amino antipyrine and phenol form red benzophenone imine under the effect of peroxidase (POD) benzophenone imine, the depth of the color of the ketone compounds is directly proportional to the content of glucose. Determine the absorbance values of the standard tube and the sample tube respectively, and then calculate the content of glucose.

TABLE 8

Influence of compositions of pieces on the mice blood glucose concentration of the hyperglycemia model

| | | Dose (medicinal | Blood glucose level/(mmol/l) | | | |
|---|---|---|---|---|---|---|
| | Quantity | material g/20 g) | 7 d | 14 d | 21 d | 28 d |
| High dose of pieces | 11 | 0.4 | 17.81 ± 5.43 | 18.79 ± 5.62 | 18.56 ± 5.05* | 18.37 ± 6.68* |
| Medium dose of pieces | 11 | 0.2 | 16.61 ± 4.98 | 17.36 ± 5.53 | 19.52 ± 6.68* | 19.46 ± 7.04* |

TABLE 8-continued

Influence of compositions of pieces on the mice blood glucose concentration of the hyperglycemia model

| | Quantity | Dose (medicinal material g/20 g) | Blood glucose level/(mmol/l) | | | |
|---|---|---|---|---|---|---|
| | | | 7 d | 14 d | 21 d | 28 d |
| Low dose of pieces | 12 | 0.1 | 16.45 ± 4.95* | 18.92 ± 6.64 | 19.79 ± 8.15* | 20.05 ± 6.56* |
| Model group (Physiological saline) | 12 | 0.4 ml | 20.41 ± 5.66 | 21.80 ± 4.96 | 26.93 ± 2.84 | 28.63 ± 4.51 |
| Positive group (Acarbose) | 12 | 0.5 mg | 19.23 ± 7.54 | 18.00 ± 6.99 | 19.99 ± 6.69 | 22.81 ± 7.72 |
| Blank control group (Physiological saline) | 12 | 0.4 ml | 5.15 ± 1.58 | 7.99 ± 1.48 | 7.43 ± 1.47 | 8.08 ± 1.99 |

Note:
Compared with the model group, *P is less than or equal to 0.05, with a significant difference.

The above table shows that, the high, medium and low dose of the pieces and the positive group has a hypoglycemic effect.

Embodiment 8: Method of Preparing the *Polygonum capitatum* Antidiabetic Extract Oral Liquid 1) Centrifuge (1000 r/min) any of the *Polygonum capitatum* extract obtained in the Embodiment 1-4 in for 15 min, the supernatant shall be retained for further use;
2) Take the supernatant obtained in step 1), use citric acid and sodium carbonate to adjust its pH to 5, add preservatives potassium sorbate with 0.05% the weight of supernatant, later use the distilled water to prepare the liquid medicine: weight ratio of 1:1, shake evenly and filter.
3) Put the stipulate liquid obtained into the sterilized dry oral liquid bottle, seal it adequately;
4) Sterilize the oral liquid obtained in step 3) at 100° C., 30 to 40 minutes.

Embodiment 9: Method of Preparing the *Polygonum capitatum* Hypoglycemic Extract Oral Liquid 1) Centrifuge (1200 r/min) any of the *Polygonum capitatum* extract obtained in the Embodiment 1-4 in for 10 min, the supernatant shall be retained for further use;
2) Take the supernatant obtained in step 1), use citric acid and sodium carbonate to adjust its pH to 3.8, add preservatives potassium sorbate with 0.06% the weight of supernatant, later use the distilled water to prepare the liquid medicine: weight ratio of 1:1, shake evenly and filter;
3) Put the stipulate liquid obtained into the sterilized dry oral liquid bottle, seal it adequately;
4) Sterilize the oral liquid obtained in step 3) at 100° C., 30 to 40 minutes.

Embodiment 10: Method of Preparing the *Polygonum capitatum* Hypoglycemic Extract Oral Liquid 1) 1) Centrifuge (800 r/min) any of the *Polygonum capitatum* extract obtained in the Embodiment 1-4 in for 20 min, the supernatant shall be retained for further use;
2) Take the supernatant obtained in the step 1), use citric acid and sodium carbonate to adjust its pH to 6, add preservatives potassium sorbate with 0.04% the weight of supernatant, later use the distilled water to prepare the liquid medicine: weight ratio of 1:1, shake evenly and filter;
3) Put the stipulate liquid obtained into the sterilized dry oral liquid bottle, seal it adequately;
4) Sterilize the oral liquid obtained in the step 3) at 100° C., 30 to 40 minutes.

Test Case 6: Testing the Efficacy of the *Polygonum capitatum* Hypoglycemic Extract Oral Liquid Carry out the test as same efficacy trials in the test case 5, of the *Polygonum capitatum* hypoglycemic extract oral liquid, the final results are shown in Table 9.

TABLE 9

Influence of oral liquid compositions on the blood glucose concentration of hyperglycemia model mice

| Group | Quantity | Dose (medicinal material g/20 g) | Blood glucose level/(mmol/l) | | | |
|---|---|---|---|---|---|---|
| | | | 7 d | 14 d | 21 d | 28 d |
| High dose of oral liquid | 12 | 0.4 | 17.63 ± 7.10 | 18.26 ± 7.28 | 18.82 ± 8.88* | 19.90 ± 10.11 |
| Medium dose of oral liquid | 12 | 0.2 | 17.81 ± 5.43 | 20.73 ± 5.62 | 20.71 ± 5.05* | 19.37 ± 6.68* |
| Low dose of oral liquid | 12 | 0.1 | 18.11 ± 4.98 | 19.13 ± 5.53 | 20.52 ± 6.68* | 20.18 ± 7.04* |
| Model group (Physiological saline) | 12 | 0.4 ml | 20.41 ± 5.66 | 21.80 ± 4.96 | 26.93 ± 2.84 | 28.63 ± 4.51 |
| Positive group (Acarbose) | 12 | 0.5 mg | 19.23 ± 7.54 | 18.00 ± 6.99 | 19.99 ± 6.69 | 22.81 ± 7.72 |
| Blank control group (Physiological saline) | 12 | 0.4 ml | 5.15 ± 1.58 | 7.99 ± 1.48 | 7.43 ± 1.47 | 8.06 ± 1.99 |

The above table shows that, the high, medium and low dose of the oral liquid, and the positive group have a hypoglycemic effect.

Embodiment 11: Method of Preparing the *Polygonum capitatum* Hypoglycemic Extract Capsule 1) Dry the *Polygonum capitatum* extract obtained in the Embodiment 1-4 to prepare the *Polygonum capitatum* extract powder;

2) Mix the 15 g microcrystalline cellulose, 3.75 g polyvinylpyrrolidone K30, 1.25 g low density hydroxypropyl cellulose and 80 g *Polygonum capitatum* extract powder, fully and evenly stir the mixture, place in a water bath to heat up it.

3) Add 65° C. hot water, and then continuously knead to preparation the soft material, until the color of the mixture is uniform and soft material has a suitable moisture, achieves the state of "lumping by one hand, scattered by a gentle pinch";

4) Pelletize with the extrusion spheronization, the extruder orifice diameter is 1 mm, the extrusion speed is set to 40 rpm/min, the spheronization speed is 1400 rpm/min, the spheronization time is 5 min, the micro pill round up shall be placed on the 40° C. oven drying for 12 h, and then sieve to obtain the regular pills;

5) The pills shall be filled No. 0 capsule filling board into the capsules, which are the *Polygonum capitatum* hypoglycemic extract capsules obtained.

Embodiment 12: Method of Preparing the *Polygonum capitatum* Hypoglycemic Extract Capsules 1) Dry the *Polygonum capitatum* extract obtained in the Embodiment 1-4 to prepare the *Polygonum capitatum* extract powder;

2) Mix the 45 g microcrystalline cellulose, 3 g polyvinylpyrrolidone K30, 2 g low density hydroxypropyl cellulose and 50 g *Polygonum capitatum* extract powder, fully and evenly stir the mixture, place in a water bath to heat up it.

3) Add 60° C. hot water, and then continuously knead to preparation the soft material, until the color of the mixture is uniform and soft material has a suitable moisture, achieves to the state of "lumping by one hand, scattered by a gentle pinch";

4) Pelletize with the extrusion spheronization, the extruder orifice diameter is 1 mm, the extrusion speed is set to 30 rpm/min, the spheronization speed is 1000 rpm/min, the spheronization time is 4 min, the micro pill round up shall be placed on the 40° C. oven drying for 12 h, and then sieve to obtain the regular pills;

5) The pills shall be filled No. 0 capsule filling board into the capsules, which are the *Polygonum capitatum* hypoglycemic extract capsules obtained.

Embodiment 13: Method of Preparing *Polygonum capitatum* Hypoglycemic Extract Capsule 1) Dry the *Polygonum capitatum* extract obtained in the Embodiment 1-4 to prepare the *Polygonum capitatum* extract powder;

2) Mix the 15 g microcrystalline cellulose, 10 g polyvinylpyrrolidone K30, 5 g low density hydroxypropyl cellulose and 70 g *Polygonum capitatum* extract powder, fully and evenly stir the mixture, place in a water bath to heat up it.

3) Add 70° C. hot water, and then continuously knead to preparation the soft material, until the color of the mixture is uniform and soft material has a suitable moisture, achieves to the state of "lumping by one hand, scattered by a gentle pinch";

4) Pelletize with the extrusion spheronization, the extruder orifice diameter is 1 mm, the extrusion speed is set to 50 rpm/min, the spheronization speed is 1200 rpm/min, the spheronization time is 3 min, the micro pill round up shall be placed on the 40° C. oven drying for 12 h, and then sieve to obtain the regular pills;

5) The pills shall be filled No. 0 capsule filling board into the capsules, which are the *Polygonum capitatum* hypoglycemic extract capsules obtained.

Test Case 7: Testing the Efficacy of the *Polygonum capitatum* Hypoglycemic Extract Capsule Carry out the test as same efficacy trials in the test case 5, of the *Polygonum capitatum* hypoglycemic extract capsules, the final results are shown in Table 10.

TABLE 10

Influence of compositions of the capsule on the blood glucose concentration of hyperglycemia model mice.

| Group | Quantity | Dose medicinal material g/20 g) | Blood glucose level | | | |
|---|---|---|---|---|---|---|
| | | | 7 d | 14 d | 21 d | 28 d |
| High dose of capsule | 12 | 0.4 | 17.81 ± 5.43 | 20.73 ± 5.62 | 20.71 ± 5.05* | 19.37 ± 6.68* |
| Medium dose of capsule | 12 | 0.2 | 18.11 ± 4.98 | 19.13 ± 5.53 | 20.52 ± 6.68* | 20.18 ± 7.04* |
| Low dose of capsule | 13 | 0.1 | 15.62 ± 4.95* | 18.92 ± 6.64 | 19.79 ± 8.15* | 18.05 ± 7.46* |
| Model group (Physiological saline) | 12 | 0.4 ml | 20.41 ± 5.66 | 21.80 ± 4.96 | 26.93 ± 2.84 | 28.63 ± 4.51 |
| Positive group (Acarbose) | 12 | 0.5 mg | 19.23 ± 7.54 | 18.00 ± 6.99 | 19.99 ± 6.69 | 22.81 ± 7.72 |
| Blank control group (Physiological saline) | 12 | 0.4 ml | 5.15 ± 1.58 | 7.99 ± 1.48 | 7.43 ± 1.47 | 8.08 ± 1.99 |

The above table shows that, the high, medium and low dose of the capsules and the positive group has a hypoglycemic effect.

Embodiment 14: Preparation of *Polygonum capitatum* Hypoglycemic Extract Granules 1) Dry the *Polygonum capitatum* extract obtained in the Embodiment 1-4 to prepare the *Polygonum capitatum* extract powder;

2) Mix the *Polygonum capitatum* extract powder obtained in the step 1), dextrin and the adequate amount of water, the weight ratio of the said *Polygonum capitatum* extract and dextrin is 2:1, dry it, and crush;

3) Add ethanol into the mixture obtained in the step 2), the weight ration of the material and the ethanol with a concentration of 50% is 5:1, granulate, bag it, which is the *Polygonum capitatum* hypoglycemic extract granule obtained.

Embodiment 15: Preparation of the *Polygonum capitatum* Hypoglycemic Extract Granules 1) Dry the *Polygonum capitatum* extract obtained in the Embodiment 1-4 to prepare the *Polygonum capitatum* extract powder;

2) Mix the *Polygonum capitatum* extract powder obtained in the step 1), dextrin and the adequate amount of water, the weight ratio of the said *Polygonum capitatum* extract and dextrin is 1.5:1, dry it, and crush;

3) Add ethanol into the mixture obtained in the step 2), the weight ration of the material and the ethanol with a concentration of 50% is 4:1, granulate, bag it, which is the *Polygonum capitatum* hypoglycemic extract granule obtained.

Embodiment 16: Preparation of the *Polygonum capitatum* Hypoglycemic Extract Granules 1) Dry the *Polygonum capitatum* extract obtained in the Embodiment 1-4 to prepare the *Polygonum capitatum* extract powder;

2) Mix the *Polygonum capitatum* extract powder obtained in the step 1), dextrin and the adequate amount of water, the weight ratio of the said *Polygonum capitatum* extract and dextrin is 2.5:1, dry it, and crush;

3) Add ethanol into the mixture obtained in the step 2), the weight ration of the material and the ethanol with a concentration of 50% is 6:1, granulate, bag it, which is the *Polygonum capitatum* hypoglycemic extract granule obtained.

Test Case 8: Testing the Efficacy of Extract of *Polygonum capitatum* Hypoglycemic Granules Carry out the test as same efficacy trials in the test case 5, of the *Polygonum capitatum* hypoglycemic extract capsules, the final results are shown in Table 11.

What is claimed:

1. A method for obtaining a *Polygonum capitatum* extract consisting essentially of:
    a) drying *Polygonum capitatum* and then adding 55%-65% ethanol to produce a *Polygonum capitatum*/ethanol mixture;
    b) extracting the *Polygonum capitatum*/ethanol mixture via reflux to form a *Polygonum capitatum*/ethanol extract liquid and a *Polygonum capitatum*/ethanol extract residue and then filtering and concentrating the *Polygonum capitatum*/ethanol extract liquid to obtain a concentrated *Polygonum capitatum*/ethanol extract;
    c) extracting the *Polygonum capitatum*/ethanol extract residue with water to produce a *Polygonum capitatum* water extract, and then filtering and concentrating the *Polygonum capitatum* water extract to obtain a concentrated *Polygonum capitatum* water extract; and
    d) combining the concentrated *Polygonum capitatum*/ethanol extract and the concentrated *Polygonum capitatum* water extract, and then combining the two extracts together to obtain the *Polygonum capitatum* extract, wherein the *Polygonum capitatum* is fresh and is kept at a temperature of −55° C. to −45° C. and at a pressure of 15 Pa~25 Pa for more than 18 hours or continuously drying the fresh *Polygonum capitatum* at a temperature of 40° C.-50° C. for more than 36 hours, the amount of the ethanol used is 22-26 times the amount of the dried *Polygonum capitatum*, the dried *Polygonum capitatum* is soaked for 20-40 minutes, and extracted three times for one-two hours each time.

2. The method of claim 1, wherein the extraction of the *Polygonum capitatum*/ethanol extract residue with water is performed two times, wherein the first time water is added at 10-14 times the amount of the *Polygonum capitatum*/ethanol extract residue and is extracted for 1 to 2 hours to produce a first water extract and then the second time adding water at 8-12 times the amount of the *Polygonum capitatum*/ethanol extract residue and extracting for 0.5 to 1 hours to produce a second water extract, and then combining the first water extract and the second water extract and then concentrating them to obtain the concentrated water extract.

TABLE 11

Influences of composition of the granule on the blood glucose concentration of hyperglycemia model mice.

| | Quantity | Dose (medicinal material g/20 g) | Blood glucose level | | | |
|---|---|---|---|---|---|---|
| | | | 7 d | 14 d | 21 d | 28 d |
| High dose of granules | 11 | 0.4 | 17.81 ± 5.43 | 18.79 ± 5.62 | 18.56 ± 5.05* | 18.37 ± 6.68* |
| Medium dose of granules | 11 | 0.2 | 16.61 ± 4.98 | 17.36 ± 5.53 | 19.52 ± 6.68* | 19.46 ± 7.04* |
| Low dose of granules | 12 | 0.1 | 16.45 ± 4.95* | 18.92 ± 6.64 | 19.79 ± 8.15* | 20.05 ± 6.56* |
| Model group (Physiological saline) | 12 | 0.4 ml | 20.41 ± 5.66 | 21.80 ± 4.96 | 26.93 ± 2.84 | 28.63 ± 4.51 |
| Positive group (Acarbose) | 12 | 0.5 mg | 19.23 ± 7.54 | 18.00 ± 6.99 | 19.99 ± 6.69 | 22.81 ± 7.72 |
| Blank control group (Physiological saline) | 12 | 0.4 ml | 5.15 ± 1.58 | 7.99 ± 1.48 | 7.43 ± 1.47 | 8.08 ± 1.99 |

Note:
Compared with the model group, *P is less than or equal to 0.05, has a significant difference.

The table shows that, the high, medium and low dose of the granules, and the positive group has a hypoglycemic effect.

* * * * *